United States Patent [19]

Lindemann

[11] Patent Number: 4,463,522

[45] Date of Patent: Aug. 7, 1984

[54] SYSTEM AND APPARATUS FOR PLANT TISSUE CULTURE PROPAGATION

[76] Inventor: Eckhart Lindemann, 1318 State St., Ithaca, N.Y. 14850

[21] Appl. No.: 282,788

[22] Filed: Jul. 13, 1981

Related U.S. Application Data

[62] Division of Ser. No. 060,539, Jul. 26, 1979.

[51] Int. Cl.$^3$ ............................................. A01G 31/00
[52] U.S. Cl. ........................................... 47/58; 47/17
[58] Field of Search ........................... 47/1.1, 58, 17; 435/240–241, 260, 284–287, 296–298, 299–301, 310–311, 313

[56] References Cited

PUBLICATIONS

Clonal Propagation of Ginger . . . , Hosoki et al., Hortscience, vol. 12(5), Oct. 1977, pp. 451–452.

Primary Examiner—Robert E. Bagwill

[57] ABSTRACT

This invention relates to a method for rapid plant propagation through tissue culture, which method comprises commutating a sterile explant to provide a multiplicity of explant particles each capable of reproducing the parent plant, suspending the reproducing explant particles in a fluid medium having a viscosity sufficiently high to prevent rapid settling of the explant particles, aseptically dispensing said suspended explant particles at spaced intervals into a presterilized growth supporting bed comprising a natural or synthetic soil mix or a gelled growth supporting substrate, such as agar; aseptically enclosing the resultant reproducing explant particle inoculated bed in a light transparent, moisture retaining plant growth space providing envelope, allowing propagation of rooted plants from said explant particles, and then hardening off the resultant plants by providing an opening in said envelope of a size sufficient to allow loss of humidity from the envelope at a rate sufficiently slow to prevent irreversible drying of leaves or a substantial degree of shock. The invention also relates to the apparatus employed in the process.

5 Claims, 4 Drawing Figures

SYSTEM AND APPARATUS FOR PLANT TISSUE CULTURE PROPAGATION

This is a division, of application Ser. No. 060,539, filed July 26, 1979.

BACKGROUND OF THE INVENTION

Tissure culture propagation of plants is known in the art. For Example, T. Murashige, *Ann. Rev. Plant Physiol.*, 25, 135-166 (1974) reviews the art with the citations of 256 references.

J. F. Knauss, *Proc. Fla. State Hort. Soc.*, 89, 363-365 (1976), has described a partial tissue culture method of propagating selected Ferns from spores.

The cloning or tissue culturing of plants has also caught the public interest as demonstrated by newspaper reports i.e. Koon, Wall Street Journal of Aug. 7, 1978 and Seibert, The New York Times, Aug. 6, 1978.

A major problem in providing relatively labor free, relatively high yield tissue culture derived plants is the number of individual transfers and treatments required in taking a growth point-containing plant tissue particle through its development to a hardened-off plant capable of surviving a typical plant nursery environment.

DESCRIPTION OF THE INVENTION

The invention relates to a system for plant tissue culture which allows a relatively small amount of labor to provide a large number of plants. The invention also relates to novel steps within the overall process as well as to apparatus employed in the system.

DETAILED DESCRIPTION OF THE INVENTION

The system and apparatus of this invention are adapted to provide tissue culture propagation of virtually any plant susceptible to tissue culture propagation.

Figure 1:
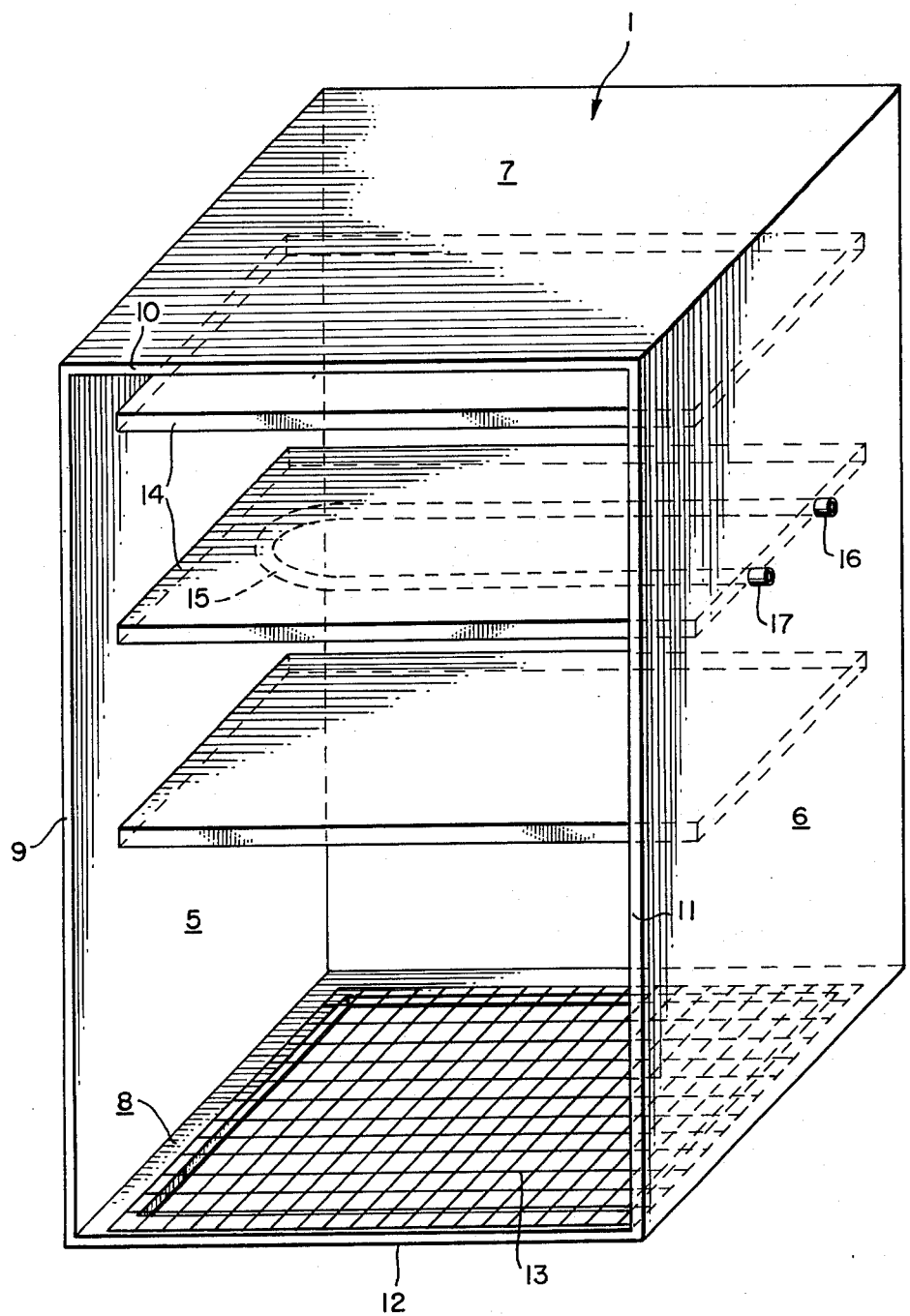
FIG. 1 is an overall view of a sterilization box structure employed in the system of the invention with front wall removed.
Figure 2:
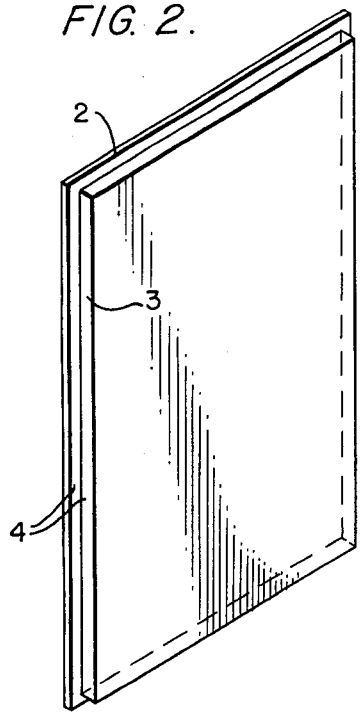
FIG. 2 is the front wall of the box shown in FIG. 1. The removable wall provides a sealable access means into the box.

In the system of the invention a growth medium sterilizing apparatus comprises (with reference to FIGS. 1 and 2) a sterilization box structure 1 (shown in FIG. 1 with the front 2, shown in FIG. 2 removed) which provides an enclosure into which entry of a microbiological contaminant can be retarded. The box structure is preferably formed from metal, e.g. aluminum. The box structure is provided with a sealable access means, sealable against the box body, e.g. removable vertical wall 2, having a flange 3, and having a microbiological contamination entry retardant sealing means (i.e. cotton, not shown) about said flange in area 4; said flange adapted to fit inside walls 5 and 6, top 7 and bottom 8 so that said sealing means engages edges 9, 10, 11 and 12 to form the enclosure. Alternatively, for example, the box could contain fixed walls, with a sealable door providing access means. The box is operably associated with a microbiological contaminant entry filter means (cotton, not shown) for example, secured to a wire mesh 13 which comprises the bottom of the box, to allow passage of steam or air into and out of the sterilization box, while retarding microbiological contamination of growth medium after sterilization within the box. The interior of the box contains growth medium unit support means, e.g. shelves 14, adapted to allow circulation of steam or air, entering the box through said filter means, to growth medium units supported thereon. In a preferred embodiment, the sterilization box contains a heat exchange means whereby the elevated temperature of growth medium containing units contained in the box after sterilization can be lowered. The most efficient heat exchange means is a heat exchange means operably associated with the growth medium unit support means, for example a cooling coil 15 passing through the shelf 14 and connected to a coolant supply through coolant entry pipe 16 and coolant exit pipe 17.

Figure 3:
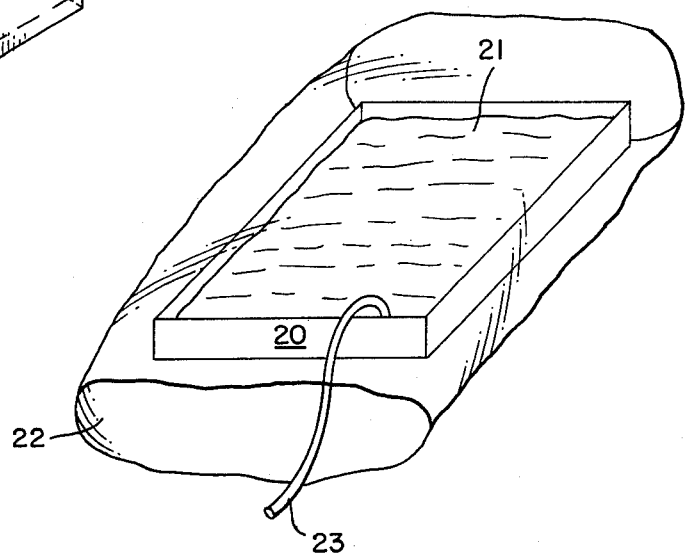
FIG. 3 is a plant growth tray inside a light transmitting plastic bag.

In the presently preferred embodiment, (with reference to FIG. 3) the growth medium unit comprises a liquid retentive tray 20, preferably aluminum containing a suitable growth medium 21. The tray is contained in a flexible moisture impervious, growth light transmitting envelope, for example, a polypropylene bag of sufficient size to allow plant growth when closed about the tray. The envelope has an opening 22 through which there is positioned a closure prevention means 23, which prevents the opening 22 from completely sealing when pressure within the envelope is reduced or external pressure increased. In a preferred embodiment, the closure preventing means 23 is also a wick means, e.g. a string which has one end buried within the growth medium with the other end passing out through the opening 22. As is explained hereinafter, the wick means, after it has served its purpose as a closure prevention means, can be employed in a latter stage as a wick means by inserting the wick end, previously passing through the opening 22, under tray 20 prior to the deliberate closure of the envelope so as to absorb any condensation which collects at the bottom of the envelope after closure and return it to the growth medium.

In operation, the tray 20 is filled with a suitable sterilizable growth medium adapted, on the one hand, to support differentiating growth of the plant growth point to form a plantlet, and which, on the other hand, is adapted to support maintenance of a hardened-off plantlet prior to transplanting. Typically the growth medium comprises soil, sand, humus, artificial soils or semi-solid gelled tissue culture media, such as supplemented agar or agar substitutes, optionally supplemented with nutrients and plant growth regulators. The growth medium also comprises, if necessary, sufficient added fertilizer to support the plant through growth until transplanting. If desired, the fertilizer or other supplements can be added in conjunction with the inoculation of growth point containing plant particles described hereinafter.

In the presently preferred embodiment, the growth medium filled tray is placed in the envelope, for example, a polypropylene bag which resists sterilization temperatures and a closure prevention means positioned through the mouth of the bag. This assembly comprises the growth medium unit. Alternatively, the growth medium unit can comprise the growth medium filled tray which is enclosed into a suitable envelope, under sterile conditions, subsequent to sterilization of the unit.

A multiplicity of the growth medium units are placed on the shelves within the box in a manner to assure relatively uniform exposure to steam in an autoclave. The access opening in the box is then sealed. One or more boxes are placed in a steam autoclave and autoclaved, for example, at 121° C. for 25 minutes, 15 psig. Steam enters the box and air escapes through the filtered openings in the bottom of the box, followed by a rapid exhaust to assist in removing air from the system. At this point, the closure prevention means prevents the bag from completely closing, thereby allowing the next actual sterilizing cycle to sterilize the contents of the bag. As soon as the pressure in the autoclave has reached ambient pressure, the units are again autoclaved at 121° C. for 25 minutes 15 psig. Upon completion of this cycle, again preferably terminated by a rapid exhaust of the autoclave, the boxes are allowed to cool, if desired, with the aid of the heat exchange means such as described above.

The box is then opened in a microbiologically clean environment. The plastic bag is opened and, employing sterile technique, a suspension of reproducing sterile plant particles is pipetted into regularly spaced apart locations (locations 24-35 in FIG. 4) on the growth medium. A wick means, such as 23 previously discussed, is positioned with one end in growth medium and the other end underneath the tray. The bag is then closed in a manner which retards microbiological contamination, for example, by placing a cotton ball into the opening of the bag (to allow $CO_2$ to enter) with the bag mouth sealed about the cotton ball, by means of a rubber band. At some point prior to closure, sufficient moisture and supplements if desired are added to the growth medium unit to allow the plants to grow without further additions of water. In the alternative embodiment the envelope free unit, after inoculation, is then placed into an envelope, under sterile conditions, and the resulting unit treated as above.

The resultant closed inoculated growth medium units are placed in a culture environment e.g. under controlled flourescent light or natural light and kept there at a growth promoting temperature until the resultant plants are large enough to be shipped and hardened off.

When the plants have grown to sufficient size to become items of commerce, the cotton plug is removed and the bag is closed again, as by the use of a rubber band. In accordance with the system of this invention the nursery man can then acclimatize or harden off the plants without misting or other labor intensive control intensive techniques frequently previously used. Initially, the package should be kept from all direct sunlight. As the plants have been grown in the trays within the package, they have a well developed and undisturbed root system. When hardening off is desired a hole is cut in the top of the envelope of a size sufficient to allow reduction of the relative humidity within the envelope (near 100% initially) at a rate insufficient to cause irreversible drying of leaves or shock, while gradually providing higher light intensity after about one week. The exact optimum size of the hole in the envelope will depend, in part, on the ambient relative humidity. In low relatively humidity situations a smaller hole is preferred, which can be increased in size to speed the process after about one week. The gradual disappearance of condensation inside the envelope is some indication as to the progress of the acclimation. Usually after about one or more weeks the envelope can be removed and the plants transplanted or grown on (preferably after creating drain holes in tray). Alternatively, if moisture and light are controlled the plants can be transplanted immediately.

The nursery man acquires substantial flexibility with this acclimation route. Some light acclimation can be accomplished with the bag still sealed. Transplanting can be done as working time and space permit, with the acclimation schedule adapted accordingly. Plants can be held, as received, in the sealed envelopes for an extended period by simply keeping the packages in a well shaded location.

In variations of the above system, where the autoclave is so designed and so positioned that sterile growth media containing trays can be transferred to a sterile work area without contamination in the absence of the envelope, the envelope first can be placed about the tray after inoculation with the growth point containing plant particle, for example, using a preformed sterile bag or by forming a heat sealed envelope from sterile plastic film in situ. The remainder of the system is then followed. In additional variations, rather than employing a gas permeable opening in the mouth of the envelope, e.g. a cotton plug, the envelope can be sealed gas tight, optionally after creating a modified atmosphere, for example, enriched in $CO_2$ inside the envelope. Likewise, whether the envelope is completely closed to gas exchange (e.g. heat sealed) or not (e.g. cotton plugged), if desired, the atmosphere within the envelope can be adjusted at a given time by the deliberate addition of a desired gas, e.g. $CO_2$, if necessary by forming temporary opening in the envelope and/or by adjusting the external atmosphere, or by piping the desired gas into the envelope under pressure. If desired, the atmosphere inside the envelope can be controlled in whole or in part by the selection of an envelope formed from a film having a predetermined desirable gas permeability.

The inoculant suspension of sterile plant particles capable of reproducing the parent plant is formed by suspending the reproducing plant tissue particles in a solution viscous enough to maintain the plant tissue particles in stable suspension, yet liquid enough to be readily dispensed as drops. Aqueous agar solutions are suitable viscous solutions. If desired, required fertilizer can also be added to the suspension. The oxygen content in the suspension should be maintained at a level sufficient to allow respiration of the plant tissue. The inoculant suspension concentration is adjusted such that a dispensed drop can be expected to contain at least one plant reproducing particle. This can be done by checking a drop of appropriate size under a microscope. An average of 3–4 reproducing particles will reasonably assure that at least one reproducing particle is present in any drop. The fact that several plantlets are developed at each inoculation point in the tray results in faster development due to crowding; the plantlets will reach height faster. Also the multiple growth points will later fill any given pot faster.

While the use of dispensed drops, are preferred, where desired forceps can be employed to inoculate particles into the growth medium.

The reproducing growth point containing tissue particles can be obtained in various ways, depending on the plant species in question. One skilled in the art will recognize whether for a particular plant species the starting material should be obtained from yet completely undifferentiated tissue stock maintained, for example, in liquid or semi-solid tissue growth culture media or whether sterile plantlets or mature plants should be employed as the growth point containing tissue particle, or seeds in special cases.

EXAMPLE

Initial Propagation on Agar

Sterile tissue culture derived Boston ferns (less than 2" in height) were de-leaved with a scalpel and the growing points placed in a blender to which was added a 0.3% agar solution, pH 5.7, also containing a complete fertilizer, such as Murashige and Skoog. The blender was run for one or more short period of 30 seconds to cut up all large particles down to a size of about 2 mm or less.

Aluminum trays were filled with a semi-solid agar propagation medium, comprising a Murashige/Skoog salt mix plus 30 g/l sucrose, 100 mg/l inositol, 0.4 mg/l thiamine HCL and 6 g/l agar, pH 5.7. After hardening of the gel, the trays were placed into plastic bags supplied with a string along the bottom, one end of the string extending out of the bag. Twenty-four (24) such bags were placed into a sterilization box of the type shown in FIGS. 1 and 2 in eight layers.

Upon completion of the autoclaving, the sterilization box was opened under sterile conditions and the trays were inoculated with the above growth point containing solution by pouring an amount into each tray sufficient to cover the entire growth surface. The trays were closed with a cotton ball and placed in the culture room for about six weeks. In order to obtain sufficient growth points for a large planting, three or four such propagation and growing cycles precede the final planting on soil mix.

Final Planting on Soil Mix

Aluminum trays (6"×9"×1") were filled with a growth medium comprising peat and vermiculite 1:1 or similar material in varying proportions suitable for growing the plantlets and allowing good root formation. The dry mix was limed with sufficient pulverized limestone to raise the pH of the final medium to pH 6.2. Fertilizer solution, as in the Murashige/Skoog salt mix, was prepared in a large container and used to wet the soil mix to a tray weight of about 400 g, which allows sufficient moisture for the growing period of the plants Prior to filling the Aluminum trays with soil mix, a string was placed in the bottom of the tray, and extending out of the tray. The tray was placed in a polypropylene bag with the free end of the string extending out of the bag. Again 24 such bags were placed into a sterilization box and autoclaved.

Figure 4:
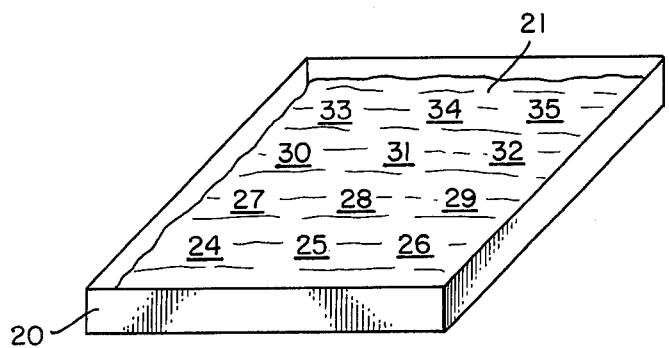
FIG. 4 is a plant growth tray containing a multiplicity of planted tissue cultured plant reproducing particles.

The sterilized box was opened under aseptic conditions and the trays were inoculated with a fern particle suspension, such as described above, with the concentration adjusted as discussed above, using a six-pronged pipette (9 rows-54 sites) such as shown in FIG. 4. The string, which previously had prevented bag closure was pushed under the tray to serve as a wick. A cotton ball was inserted into the opening in the plastic bag and the bag sealed with a rubber band. The trays were placed under fluorescent lights for three months or longer at a light/dark cycle of 16/8 hours and a light intensity of about 200 foot candles.

While the propagation of ferns has been exemplified, as previously indicated with proper selection of media the system of the present invention has broad applicability. For example, in addition to various ferns the system of the invention can be adapted to the propagation of plants such as potatoes, lilies, rubber trees, philodendrons, syngoniums, strawberries, raspberries, asparagus, grapes, peaches, redwood trees, tobacco, chrysanthemums, begonias, bromeliads, freesia, gladiolus, gerbera, orchids and any others which can be propagated by tissue culture.

While the invention and what is now considered its best embodiments have been set forth above, the invention may be practical otherwise than specifically described within the scope of the appended claims.

I claim:

1. A method for tissue culture propagation of plants which comprises:
    (a) sterilizing a plant tissue culture medium in a receptacle, said growth medium adapted to support differentiating growth of the plant tissue culture to be inoculated therein, as well as adapted to support maintenance of a hardened-off plantlet prior to transplant,
    (b) inoculating said plant tissue culture medium in said receptacle with a plant tissue culture,
    (c) enclosing said inoculated plant tissue culture medium receptacle in a plant growth light transmitting flexible plastic envelope,
    (d) maintaining said envelope under conditions which cause formation of a rooted plantlet,
    (e) hardening off said plantlet by providing an opening in said envelope of a size sufficient to allow the interior of the envelope to approach the ambient relative humidity at a rate insufficient to cause irreversible leaf drying or fatal plant shock.

2. A method of hardening off a rooted, plant tissue culture derived plantlet, being maintained in an enclosure at high relative humidity, which comprises providing an opening in said enclosure of a size sufficient to allow the interior of said enclosure to approximate the ambient relative humidity at a rate insufficient to cause irreversible leaf drying or fatal plant shock.

3. A method for tissue culture propagation of plants which comprises:
    (a) sterilizing a plant tissue culture medium in a receptacle enclosed in an open plant growth light transmitting flexible plastic envelope, said growth medium adapted to support differentiating growth of the plant tissue culture to be inoculated therein, as well as adapted to support maintenance of a hardened-off plantlet prior to transplant,
    (b) inoculating said plant tissue culture medium in said receptacle with a plant tissue culture,
    (c) sealing said envelope to retard biological contamination and maintaining said envelope under conditions which cause formation of a rooted plantlet,
    (d) hardening off said plantlet by providing an opening in said envelope of a size sufficient to allow the interior of the envelope to approach the ambient relative humidity at a rate insufficient to cause irreversible leaf drying or fatal plant shock.

4. A method as in claim 3 wherein the medium in said envelope is subjected during sterilization to multiple exposures to steam and wherein the envelope is prevented from completely closing during said multiple steam exposures by the free end of a wick means extending from said medium through the opening in said envelope and wherein the free end of said wick means is subsequently placed beneath said receptacle prior to (c).

5. In a method of tissue culture propagation of plants wherein plant tissue culture is inoculated into and propagated in a sterile growth medium to form a rooted plantlet, the improvement which comprises:
(a) enclosing a receptacle containing said inoculated sterile growth medium in a plant growth light transmitting flexible plastic envelope,
(b) maintaining said envelope under conditions which cause formation of a rooted plantlet, and
(c) hardening off said plantlet by providing an opening in said envelope of a size sufficient to allow the interior of the envelope which remains about the plantlet to approach the ambient relative humidity at a rate insufficient to cause irreversible leaf drying or fatal plant shock.

* * * * *